United States Patent
Matson et al.

(10) Patent No.: US 9,005,154 B2
(45) Date of Patent: Apr. 14, 2015

(54) VALVED HEMODIALYSIS CATHETER

(75) Inventors: Scott Matson, Flower Mound, TX (US); Richard Braga, North Easton, MA (US)

(73) Assignee: Covidien LP, Mansfield, MA (US)

( * ) Notice: Subject to any disclaimer, the term of this patent is extended or adjusted under 35 U.S.C. 154(b) by 1640 days.

(21) Appl. No.: 12/239,103

(22) Filed: Sep. 26, 2008

(65) Prior Publication Data
US 2010/0081986 A1 Apr. 1, 2010

(51) Int. Cl.
- A61M 1/14 (2006.01)
- A61M 25/14 (2006.01)
- A61M 25/00 (2006.01)
- A61M 1/36 (2006.01)

(52) U.S. Cl.
CPC ....... A61M 25/0075 (2013.01); A61M 25/0074 (2013.01); A61M 25/0067 (2013.01); A61M 25/0029 (2013.01); A61M 2025/0078 (2013.01); A61M 25/003 (2013.01); A61M 2025/0031 (2013.01); A61M 2025/0037 (2013.01); A61M 2025/0039 (2013.01); A61M 2025/0076 (2013.01); A61M 1/3661 (2014.02)

(58) Field of Classification Search
CPC .......... A61M 25/003; A61M 25/0075; A61M 1/3661; A61M 2025/0031; A61M 2025/0039; A61M 2025/0076; A61M 2025/0037; A61M 25/0021; A61M 25/0029; A61M 25/0067; A61M 25/0074; A61M 2025/0078
USPC ............ 604/4.01, 6.16, 8, 27, 30, 93.01, 118, 604/119, 540, 34, 35, 43, 131, 167.03, 604/167.04, 173, 264
See application file for complete search history.

(56) References Cited

U.S. PATENT DOCUMENTS

| | | | |
|---|---|---|---|
| 4,391,276 A | 7/1983 | Lazarus et al. | |
| 4,403,983 A | 9/1983 | Edelman et al. | |
| 4,475,898 A | 10/1984 | Brodner et al. | |
| 4,493,696 A | 1/1985 | Uldall | |

(Continued)

FOREIGN PATENT DOCUMENTS

| | | | |
|---|---|---|---|
| EP | 0 299 622 A2 | 1/1989 | |
| EP | 0 299 622 A3 | 1/1989 | |

(Continued)

OTHER PUBLICATIONS

European Search Report corresponding to European Application No. 09 25 1289, completed Sep. 22, 2009; 6 pages.

(Continued)

Primary Examiner — Adam Marcetich
(74) Attorney, Agent, or Firm — John Paul Mello, Esq.

(57) ABSTRACT

A dialysis catheter includes an elongate catheter member having an outer wall member defining proximal and distal end regions and first and second longitudinal lumens. The outer member includes first and second ports in respective fluid communication with the first and second longitudinal lumens. The first opening and the first lumen define an inflow passage. The second opening and the second longitudinal lumen define an outflow passage. A valve is disposed relative to the outer member proximal of the first port. The valve is adapted to move from a closed position to an open position in response to a predetermined vacuum pressure level realized within the first longitudinal lumen to permit flow of blood through the valve and into the first longitudinal lumen. The valve may be adapted to move to the open position in the event of a luminal occlusion.

18 Claims, 11 Drawing Sheets

(56) References Cited

U.S. PATENT DOCUMENTS

| | | |
|---|---|---|
| 4,549,879 A | 10/1985 | Groshong et al. |
| 4,568,329 A | 2/1986 | Mahurkar |
| 4,583,968 A * | 4/1986 | Mahurkar ................. 604/43 |
| 4,619,643 A | 10/1986 | Bai |
| 4,626,240 A | 12/1986 | Edelman et al. |
| 4,643,711 A | 2/1987 | Bates |
| 4,671,796 A | 6/1987 | Groshong et al. |
| 4,692,141 A | 9/1987 | Mahurkar |
| 4,701,166 A | 10/1987 | Groshong et al. |
| 4,753,640 A | 6/1988 | Nichols et al. |
| 4,769,005 A | 9/1988 | Ginsburg et al. |
| 4,772,268 A | 9/1988 | Bates |
| 4,772,269 A | 9/1988 | Twardowski et al. |
| 4,795,439 A | 1/1989 | Guest |
| 4,808,155 A | 2/1989 | Mahurkar |
| 4,808,156 A | 2/1989 | Dean |
| 4,813,934 A | 3/1989 | Engelson et al. |
| 4,842,582 A | 6/1989 | Mahurkar |
| 4,895,561 A | 1/1990 | Mahurkar |
| 4,897,079 A | 1/1990 | Zaleski et al. |
| 4,961,809 A | 10/1990 | Martin |
| 4,973,319 A | 11/1990 | Melsky |
| 4,995,863 A | 2/1991 | Nichols et al. |
| 4,995,865 A | 2/1991 | Gahara et al. |
| 5,009,636 A | 4/1991 | Wortley et al. |
| 5,035,399 A | 7/1991 | Rantanen-Lee |
| 5,041,083 A | 8/1991 | Tsuchida et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,085,632 A | 2/1992 | Ikada et al. |
| 5,106,368 A | 4/1992 | Uldall et al. |
| 5,112,301 A | 5/1992 | Fenton, Jr. et al. |
| 5,135,599 A | 8/1992 | Martin et al. |
| 5,147,332 A | 9/1992 | Moorehead |
| 5,156,592 A | 10/1992 | Martin et al. |
| 5,160,325 A | 11/1992 | Nichols et al. |
| 5,167,623 A | 12/1992 | Cianci et al. |
| 5,171,218 A | 12/1992 | Fonger et al. |
| 5,188,593 A | 2/1993 | Martin |
| 5,190,520 A | 3/1993 | Fenton, Jr. et al. |
| 5,195,962 A | 3/1993 | Martin et al. |
| 5,197,951 A | 3/1993 | Mahurkar |
| 5,209,723 A | 5/1993 | Twardowski et al. |
| 5,219,335 A | 6/1993 | Willard et al. |
| 5,221,255 A | 6/1993 | Mahurkar et al. |
| 5,221,256 A | 6/1993 | Mahurkar |
| 5,224,938 A | 7/1993 | Fenton, Jr. |
| 5,250,034 A | 10/1993 | Appling et al. |
| 5,261,885 A | 11/1993 | Lui |
| 5,267,979 A | 12/1993 | Appling et al. |
| 5,304,155 A | 4/1994 | Lui |
| 5,308,338 A | 5/1994 | Helfrich |
| 5,346,471 A | 9/1994 | Raulerson |
| 5,348,536 A | 9/1994 | Young et al. |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,395,316 A | 3/1995 | Martin |
| 5,403,291 A | 4/1995 | Abrahamson |
| 5,405,341 A | 4/1995 | Martin |
| 5,451,206 A | 9/1995 | Young |
| 5,464,398 A | 11/1995 | Haindl |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,522,807 A | 6/1996 | Luther |
| 5,531,679 A | 7/1996 | Schulman et al. |
| 5,554,136 A | 9/1996 | Luther |
| 5,556,390 A | 9/1996 | Hicks |
| 5,569,182 A | 10/1996 | Twardowski et al. |
| 5,571,093 A | 11/1996 | Cruz et al. |
| D381,420 S | 7/1997 | Musgrave et al. |
| D384,411 S | 9/1997 | Musgrave et al. |
| D384,741 S | 10/1997 | Musgrave et al. |
| 5,683,640 A | 11/1997 | Miller et al. |
| 5,685,867 A | 11/1997 | Twardowski et al. |
| 5,702,365 A | 12/1997 | King |
| 5,718,678 A | 2/1998 | Fleming, III |
| 5,776,096 A | 7/1998 | Fields |
| 5,797,869 A | 8/1998 | Martin et al. |
| 5,807,311 A | 9/1998 | Palestrant |
| 5,807,329 A | 9/1998 | Gelman |
| 5,807,349 A | 9/1998 | Person et al. |
| 5,810,789 A | 9/1998 | Powers et al. |
| 5,830,184 A | 11/1998 | Basta |
| 5,830,196 A | 11/1998 | Hicks |
| 5,868,717 A | 2/1999 | Prosl |
| 5,928,203 A | 7/1999 | Davey et al. |
| 5,947,953 A | 9/1999 | Ash et al. |
| 5,961,485 A | 10/1999 | Martin |
| 5,961,486 A | 10/1999 | Twardowski et al. |
| 5,968,009 A | 10/1999 | Simán |
| 5,976,103 A | 11/1999 | Martin |
| 5,984,903 A | 11/1999 | Nadal |
| 5,989,206 A | 11/1999 | Prosl et al. |
| 5,989,213 A | 11/1999 | Maginot |
| 5,993,437 A | 11/1999 | Raoz |
| 6,001,079 A | 12/1999 | Pourchez |
| 6,004,310 A | 12/1999 | Bardsley et al. |
| 6,099,519 A | 8/2000 | Olsen et al. |
| 6,123,725 A | 9/2000 | Aboul-Hosn |
| 6,126,631 A | 10/2000 | Loggie |
| 6,146,354 A | 11/2000 | Beil |
| 6,156,016 A | 12/2000 | Maginot |
| 6,190,349 B1 | 2/2001 | Ash et al. |
| 6,190,371 B1 | 2/2001 | Maginot et al. |
| 6,206,849 B1 | 3/2001 | Martin et al. |
| 6,273,875 B1 | 8/2001 | Siman et al. |
| 6,280,423 B1 | 8/2001 | Davey et al. |
| 6,293,927 B1 | 9/2001 | McGuckin, Jr. |
| 6,293,958 B1 * | 9/2001 | Berry et al. ................. 606/191 |
| 6,342,120 B1 | 1/2002 | Basta |
| 6,346,090 B1 | 2/2002 | Liska et al. |
| 6,394,141 B2 | 5/2002 | Wages et al. |
| 6,409,700 B1 | 6/2002 | Siegel, Jr. et al. |
| 6,447,488 B2 | 9/2002 | Estabrook et al. |
| 6,461,321 B1 | 10/2002 | Quinn |
| 6,475,207 B1 | 11/2002 | Maginot et al. |
| 6,482,169 B1 | 11/2002 | Kuhle |
| 6,506,182 B2 | 1/2003 | Estabrook et al. |
| 6,579,261 B1 | 6/2003 | Kawamura |
| 6,585,705 B1 | 7/2003 | Maginot et al. |
| 6,592,542 B2 | 7/2003 | Childers et al. |
| 6,592,558 B2 | 7/2003 | Quah |
| 6,595,966 B2 | 7/2003 | Davey et al. |
| 6,620,118 B1 | 9/2003 | Prosl et al. |
| 6,638,242 B2 | 10/2003 | Wilson et al. |
| 6,692,473 B2 | 2/2004 | St. Cyr et al. |
| 6,695,832 B2 | 2/2004 | Schon et al. |
| 6,719,749 B1 | 4/2004 | Schweikert et al. |
| 6,723,084 B1 | 4/2004 | Maginot et al. |
| 6,730,096 B2 | 5/2004 | Basta |
| 6,743,218 B2 | 6/2004 | Maginot et al. |
| 6,749,580 B2 | 6/2004 | Work et al. |
| 6,758,836 B2 | 7/2004 | Zawacki |
| 6,786,884 B1 | 9/2004 | DeCant, Jr. et al. |
| 6,808,510 B1 | 10/2004 | DiFiore |
| 6,814,718 B2 | 11/2004 | McGuckin, Jr. et al. |
| 6,858,019 B2 | 2/2005 | McGuckin, Jr. et al. |
| 6,872,198 B1 | 3/2005 | Wilson et al. |
| 6,911,014 B2 | 6/2005 | Wentling et al. |
| 6,921,396 B1 | 7/2005 | Wilson et al. |
| 6,942,635 B2 | 9/2005 | Rosenblatt et al. |
| 6,942,653 B2 | 9/2005 | Quinn |
| 6,966,886 B2 | 11/2005 | Appling |
| 6,969,381 B2 | 11/2005 | Voorhees |
| 6,976,973 B1 | 12/2005 | Ruddell et al. |
| 6,986,752 B2 | 1/2006 | McGuckin, Jr. et al. |

(56) References Cited

U.S. PATENT DOCUMENTS

| | | |
|---|---|---|
| 6,991,625 B1 | 1/2006 | Gately et al. |
| 7,008,395 B1 | 3/2006 | Loggie |
| 7,008,412 B2 | 3/2006 | Maginot |
| 7,011,645 B2 | 3/2006 | McGuckin, Jr. et al. |
| 7,013,928 B2 | 3/2006 | Navis |
| 7,048,680 B2 | 5/2006 | Viole et al. |
| 7,066,914 B2 | 6/2006 | Andersen |
| 7,077,829 B2 | 7/2006 | McGuckin, Jr. et al. |
| 7,413,564 B2 | 8/2008 | Morris et al. |
| 2002/0121282 A1 | 9/2002 | McGuckin, Jr. et al. |
| 2003/0032918 A1 | 2/2003 | Quinn |
| 2003/0093029 A1 | 5/2003 | McGuckin, Jr. et al. |
| 2003/0191425 A1 | 10/2003 | Rosenblatt |
| 2004/0249337 A1 | 12/2004 | DiFiore |
| 2005/0033222 A1 | 2/2005 | Haggstrom et al. |
| 2005/0085765 A1 | 4/2005 | Voorhees |
| 2005/0090776 A1 | 4/2005 | McGuckin, Jr. et al. |
| 2005/0215978 A1 | 9/2005 | Ash |
| 2005/0228339 A1 | 10/2005 | Clark |
| 2005/0267400 A1 | 12/2005 | Haarala et al. |
| 2005/0288623 A1 | 12/2005 | Hjalmarsson |
| 2006/0004325 A1 | 1/2006 | Hamatake et al. |
| 2006/0149191 A1 | 7/2006 | DiFiore |
| 2006/0253063 A1 | 11/2006 | Schweikert |
| 2007/0100298 A1 | 5/2007 | Appling |
| 2009/0054825 A1 | 2/2009 | Melsheimer et al. |
| 2010/0069818 A1 | 3/2010 | Smouse |

FOREIGN PATENT DOCUMENTS

| | | |
|---|---|---|
| EP | 0 554 722 A1 | 8/1993 |
| EP | 0 322 225 B1 | 2/1995 |
| EP | 0 713 406 B1 | 3/1998 |
| EP | 0 864 336 A2 | 9/1998 |
| EP | 0 864 336 A3 | 3/1999 |
| EP | 0 570 530 B1 | 8/1999 |
| EP | 0 555 780 B1 | 9/1999 |
| EP | 1 595 565 A1 | 11/2005 |
| EP | 1 144 039 B1 | 12/2005 |
| EP | 2168625 | 3/2010 |
| JP | 2006-15058 | 1/2006 |
| JP | 2007-175297 A | 7/2007 |
| WO | 93/18814 | 9/1993 |
| WO | WO 95/04567 A1 | 2/1995 |
| WO | WO 97/37699 A1 | 10/1997 |
| WO | WO 98/41277 | 9/1998 |
| WO | WO 99/38550 | 8/1999 |
| WO | WO 99/65557 | 12/1999 |
| WO | WO 00/06239 A2 | 2/2000 |
| WO | WO 01/91845 A1 | 12/2001 |
| WO | WO 02/13899 A1 | 2/2002 |
| WO | WO 02/18004 A3 | 3/2002 |
| WO | WO 03/033049 A3 | 4/2003 |
| WO | WO 03/066148 A1 | 8/2003 |
| WO | WO 2004/093956 A1 | 11/2004 |
| WO | WO 2005/023336 A2 | 3/2005 |
| WO | WO 2005/077449 A1 | 8/2005 |
| WO | WO 2005/084741 A1 | 9/2005 |
| WO | WO 2006/014339 A2 | 2/2006 |
| WO | 2006/122026 | 11/2006 |

OTHER PUBLICATIONS

European Extended Search Report corresponding to European Application No. 09 17 0662, completed Jan. 11, 2010; mailed Jan. 27, 2010; 7 pages.

Official Action issued in Japan in the corresponding JP Appl. 2009-21722 dated Jul. 3, 2013.

EP Search Report from corresponding Application No. EP 12184656 dated May 11, 2012.

* cited by examiner

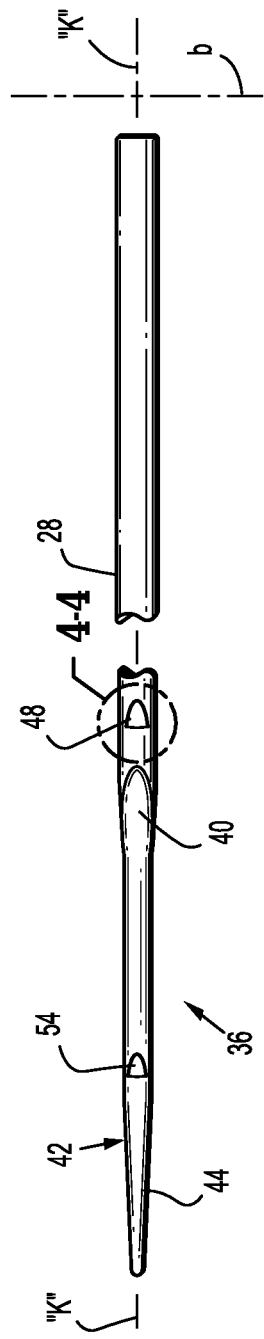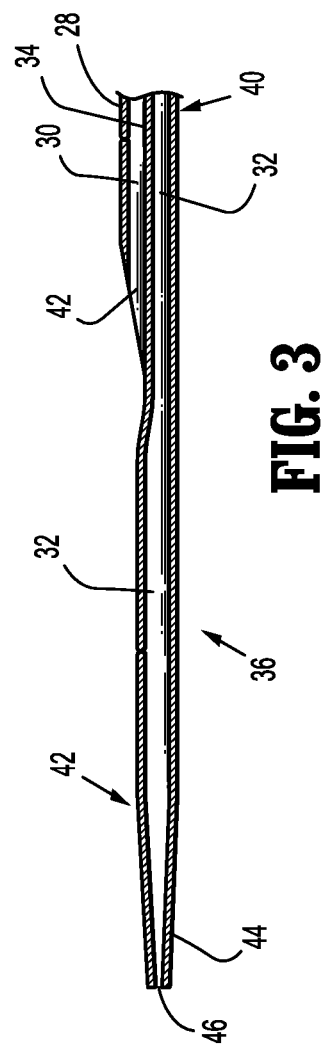

VALVED HEMODIALYSIS CATHETER

BACKGROUND

1. Technical Field

The present disclosure generally relates to a medical catheter assembly, and, more particularly relates to a hemodialysis catheter including a valve adapted to minimize the risk of occlusion of the catheter's lumens.

2. Description of the Related Art

Catheters are flexible medical instruments intended for the withdrawal and introduction of fluids relative to body cavities, ducts, and vessels. Catheter instrumentation may have particular application in a hemodialysis procedure where blood is withdrawn from a blood vessel for treatment, and subsequently returned to the blood vessel for circulation. Known hemodialysis catheters include multiple lumens, such as dual lumen or triple-lumen catheters, permitting bi-directional fluid flow within the catheter whereby one lumen is dedicated for withdrawal of blood and the other lumen is dedicated for returning the treated blood to the vessel. During an exemplary hemodialysis procedure, a multiple lumen catheter is inserted into a body and blood is withdrawn through an arterial lumen of the catheter. The removed blood is directed to a hemodialysis machine which dialyzes, or purifies, the blood to remove waste, and toxins. The dialyzed blood is returned to the patient through a venous lumen of the catheter.

One complication associated with known hemodialysis catheters concerns occlusion of the arterial lumen, particularly, positional occlusion of the tip of the catheter with the vessel wall. Positional occlusion may occur as a result of the catheter tip being pressed into a vessel wall and subsequent invagination of the vessel intima into one of the catheter lumens. When the inflow port is positionally occluded, a vacuum is created in the arterial lumen of the catheter, further drawing the vessel wall into the arterial lumen.

As a result, the clinician must address the interruption in blood flow to allow continuance of patient treatment. One solution for resolving positional occlusion is to reverse flow of the lumens of the catheter. However, reversing the flow with the lumens of the catheter involves decoupling and recoupling the lines, increases clinician handling of the catheter and increases the opportunity for microbial contamination and infection, as well as extending the time of the dialysis treatment. This results in various drawbacks including increased cost and discomfort for the patient.

SUMMARY

Accordingly, the present disclosure relates to further improvements in catheters including hemodialysis catheters. In one embodiment, a medical catheter assembly includes an elongated catheter member defining a longitudinal axis and at least one lumen for passage of fluid, and having proximal and distal end regions, and a valve disposed adjacent the distal end region of the catheter member. The valve is adapted to move from a closed position to an open position in response to a predetermined vacuum pressure level within the at least one lumen to permit flow of the fluid through the valve and into the at least one lumen. The catheter member may include a fluid port in communication with the at least one lumen and distal of the valve. The valve may be adapted to move to the open position in the event of an at least partial luminal occlusion within the at least one lumen at locations distal of the valve.

The catheter member includes an outer catheter wall with the valve being a flap defined within the outer catheter wall. The outer catheter wall and the flap may be monolithically formed. The flap may be generally triangular in shape. In the alternative, the valve may include a deformable section adjacent the distal region of the catheter member. The deformable section is configured deform upon achieving the predetermined vacuum level in the at least one lumen of the catheter member. The valve may be a one-way pressure relief member adapted to open upon achieving the predetermined vacuum level in the at least one lumen of the catheter member. The valve may be arranged to define an opening within the catheter wall when the valve is in the open position.

In one embodiment, the catheter member includes an outer catheter wall. The outer wall has inner portions defining a slit therein whereby the inner portions are adapted for relative movement to move between the open position and the closed position. The inner portions of the catheter wall may define a substantially linear slit. In the alternative, the inner portions of the catheter wall may define a substantially sinusoidal slit.

The catheter member may include a second lumen and a second valve. The second valve may be adapted to move from a closed position to an open position in response to a predetermined vacuum pressure level within the second lumen to permit flow of the fluid through the second valve and the second lumen. In this embodiment, the catheter may include a second port in fluid communication with the second lumen and distal of the second valve.

In another embodiment, a dialysis catheter includes an elongate catheter member having an outer wall member defining proximal and distal end regions and a longitudinal axis, and defining first and second longitudinal lumens. The outer member includes first and second ports in respective fluid communication with the first and second longitudinal lumens. The first opening and the first longitudinal lumen define an inflow passage for removal of blood under vacuum for circulation within a hemodialysis machine. The second opening and the second longitudinal lumen define an outflow passage for return of the blood from the hemodialysis machine. A valve is disposed relative to the outer member proximal of the first port. The valve is adapted to move from a closed position to an open position in response to a predetermined vacuum pressure level realized within the first longitudinal lumen to permit flow of blood through the valve and into the first longitudinal lumen. The valve may be adapted to move to the open position in the event of an at least partial luminal occlusion within the first longitudinal lumen at locations distal of the valve. The valve may include a flap defined in the outer wall member of the catheter member. The flap is adapted to move about a living hinge between the closed position and the open position. A second valve may be disposed relative to the outer member proximal of the second port. The second valve may be adapted to move from a closed position to an open position in response to a predetermined vacuum pressure level realized within the second longitudinal lumen to permit flow of the fluid through the second valve.

BRIEF DESCRIPTION OF THE DRAWINGS

Various embodiments of the presently disclosed catheters assemblies are described herein with references to the accompanying drawings, wherein:

FIG. 2 is a side plan view of the elongated catheter of the catheter assembly;

FIG. 3 is a side cross-sectional view of the leading end region of the elongated catheter;

DETAILED DESCRIPTION OF THE EMBODIMENTS

The exemplary embodiment(s) of the catheter and methods of use disclosed are discussed in terms of medical catheters for the administration of fluids relative to the body of a subject and, more particularly, in terms of a hemodialysis catheter. However, it is envisioned that the present disclosure may be employed with a range of catheter applications including surgical, diagnostic and related treatments of diseases, body ailments, of a subject. It is further envisioned that the principles relating to the catheter disclosed include employment with various catheter related procedures, such as, for example, hemodialysis, cardiac, abdominal, urinary, intestinal, and in chronic and/or acute applications. Moreover, the catheter can be used for administration or withdrawal of fluids such as, for example, medication, saline, bodily fluids, blood and urine.

In the discussion that follows, the term "proximal" or "trailing" will refer to the portion of a structure that is closer to a clinician, while the term "distal" or "leading" will refer to the portion that is further from the clinician. As used herein, the term "subject" refers to a human patient or other animal. The term "clinician" refers to a doctor, nurse or other care provider and may include support personnel.

Figure 1:
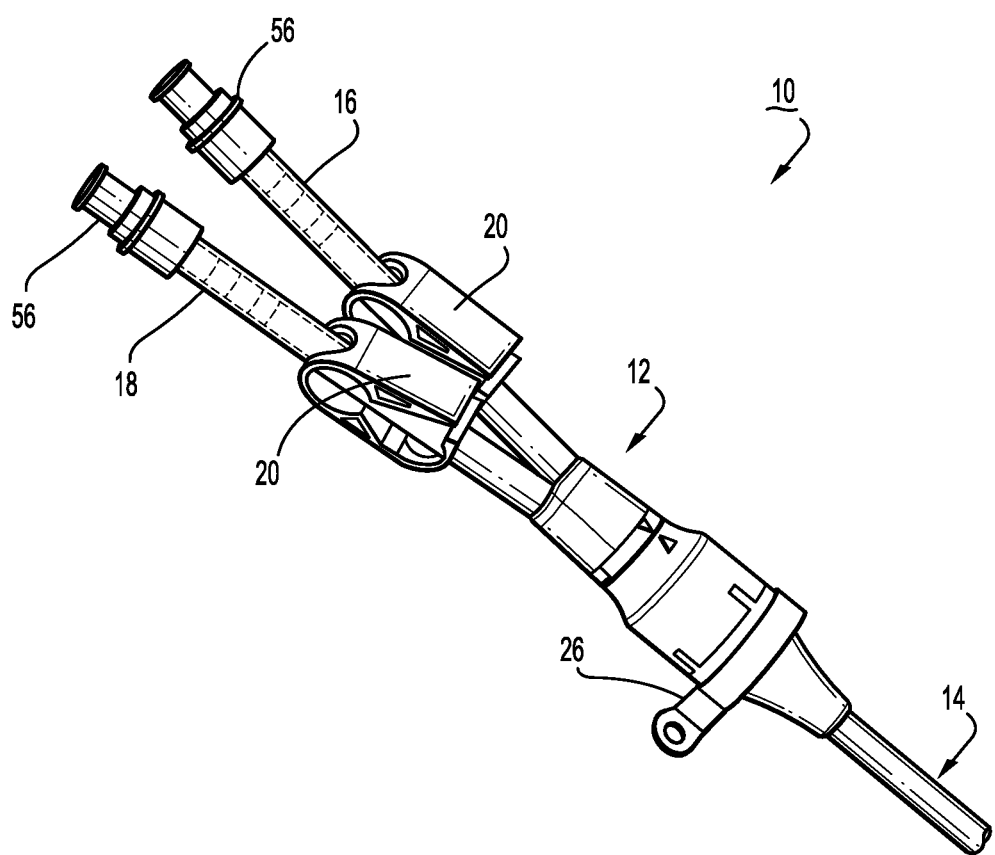
FIG. 1 is a perspective view of a catheter assembly in accordance with the principles of the present disclosure illustrating the catheter hub and the elongated catheter extending from the catheter hub.

Referring now to the drawings wherein like components are designated by like reference numerals throughout the several views, FIG. 1 illustrates in perspective view, the hemodialysis catheter 10 in accordance with the principles of the present disclosure. Catheter 10 includes several components assembled together, namely, catheter hub or housing 12, elongated catheter member 14 extending distally from the catheter hub 12 and first and second extension tubes 16, 18 extending proximally from the catheter hub 12. Catheter system 10 may further includes a pair of clamps 20 which are attached about each of extension tubes 16, 18.

Catheter hub 12 may be any housing dimensioned for engagement by the clinician, and may be formed of any suitable material including metal such as stainless steel or a compatible polymeric material. Catheter hub 12 may define elongated openings adapted to receive respective first and second extension tubes 16, 18 in secured relation therewith. In one preferred embodiment, extension tubes 16, 18 are secured within respective extension conduits (not shown) of catheter hub 12 via an interference or frictional fit, cements or adhesives. Catheter hub 12 also may define a central opening (not shown) for receiving catheter member 14. Catheter member 14 may be secured within central opening of the distal or leading section of hub 12 via any of the aforementioned methodologies.

Catheter hub 12 may further include a pair of opposed wings 26 (only one wing 26 is visible in FIG. 1) depending outwardly from the catheter hub 12. Wings 26 may serve as support elements to support first and second extension tubes 16, 18. In addition, it is contemplated that sutures may be wrapped about wings 26 to secure catheter hub 12 relative to the subject. In the alternative, wings 26 or catheter hub 12 may have an annular groove in its outer wall to receive the sutures. A suture may be wrapped within annular groove and subsequently secured relative to the subject.

Referring now to FIGS. 2-3, in conjunction with FIG. 1, elongated catheter member 14 will be discussed. Catheter member 14 defines longitudinal axis "k" and transverse axis "b" in transverse relation to the longitudinal axis "k". One suitable catheter is described in U.S. Pat. No. 4,568,329 to Mahurkar, the entire contents of which are incorporated herein by reference. Catheter member 14 may be a dual lumen catheter having outer wall 28 and first and second longitudinal lumens 30, 32 separated by a planar divider or septum wall 34 which may or may not extend the length the catheter member 14. Each of the first and second longitudinal lumens 30, 32 may define an oblong, kidney-shaped, or D-shaped opening in cross-section. Other lumen arrangements are also envisioned including circular, pie shaped etc. Coaxial lumens are also envisioned. Catheter member 14 may also include a guidewire lumen for reception and passage of a guidewire utilized to facilitate entry of the catheter member 14 within the vascular organ. Alternatively, one of first and second longitudinal lumens 30, 32 also may serve as the guidewire lumen in addition to its functioning to withdraw or deliver fluids. As a further embodiment, although hemodialysis catheter 10 is represented as a dual lumen catheter, single or triple lumen catheters are also envisioned.

With continued reference to FIGS. 1-3, catheter member 14 includes leading end region 36 which is introduced within the subject, i.e., through the vascular organ. In the illustrated embodiment, leading end region 36 may be circular in cross-section over first proximal section 40 of the leading end region 36 and defines inlet opening 42 in fluid communication with longitudinal lumen 30. Leading end region 36 further may define second distal section 44 extending beyond first proximal section 40 and enclosing longitudinal lumen 32. Second distal section 42 may be circular in cross section and have conical catheter tip 44 extending to outlet opening 46. In a hemodialysis procedure, inlet opening 42 draws the blood for processing through longitudinal lumen 30 with the processed blood being returned through longitudinal lumen 32 and out through outlet opening 46 to return the blood upstream into circulation.

Figure 4:
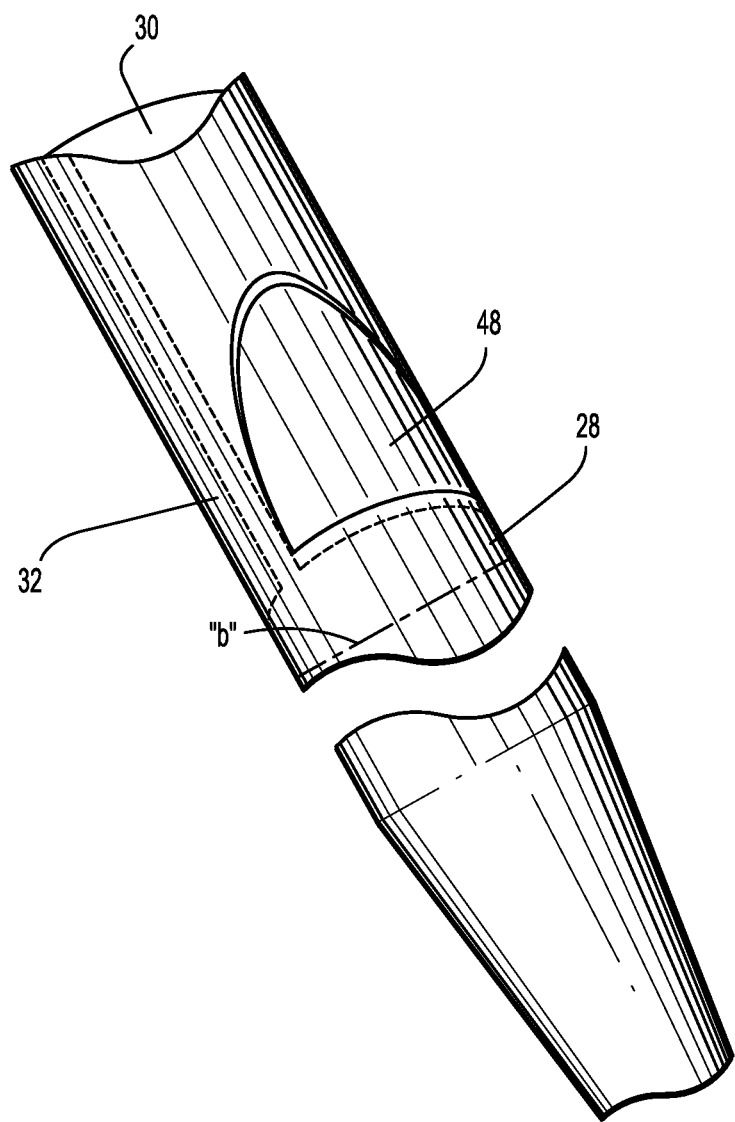
FIG. 4 is an enlarged isolated view in perspective of the area of detail 4-4 indicated in FIG. 2 depicting the valve in a closed position.
Figure 5:
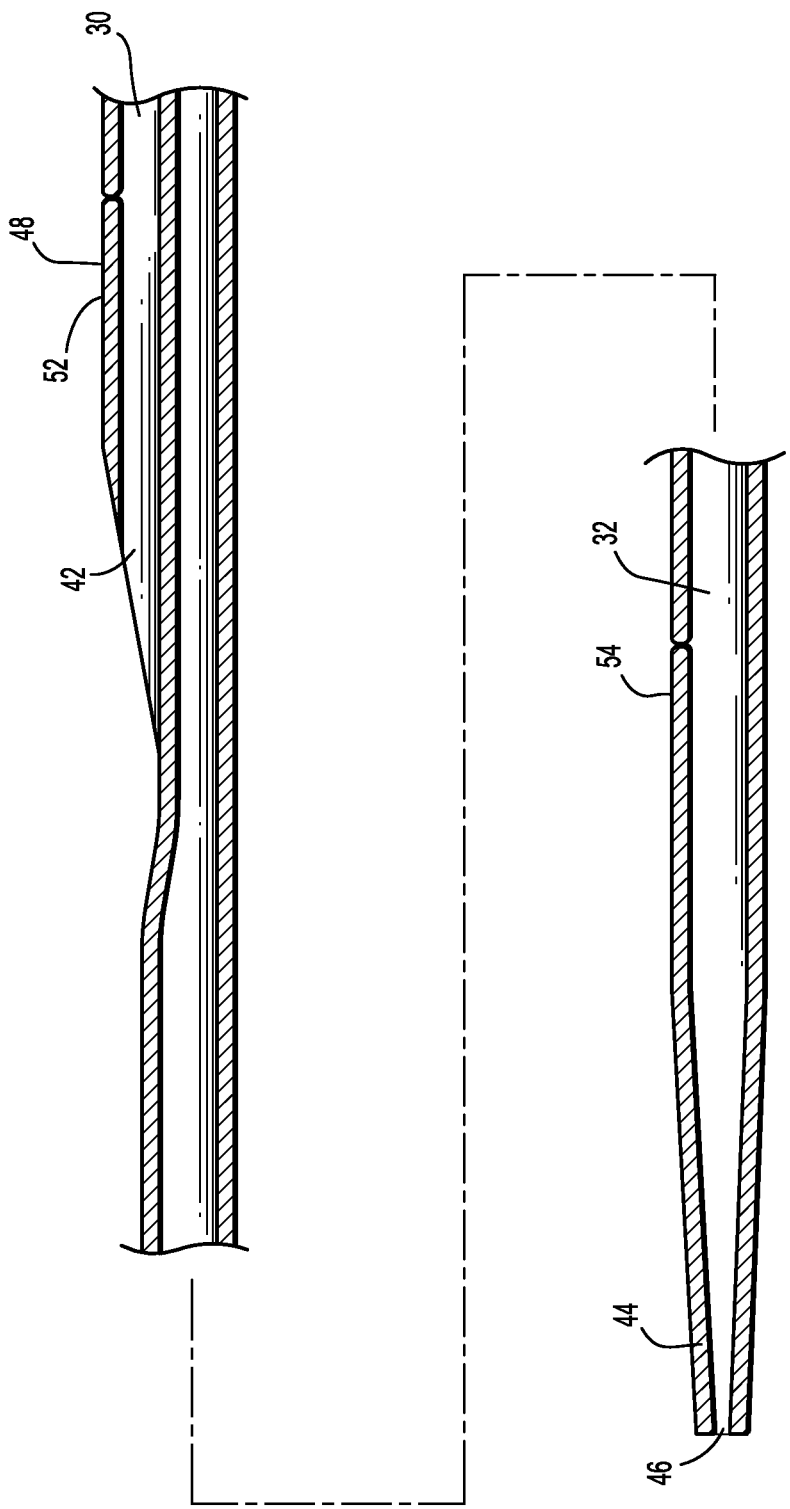
FIG. 5 is an enlarged cross-sectional view of the leading end region of the elongated catheter illustrating the valve(s) in a closed position.

With reference to FIGS. 3-5, leading end region 36 of catheter member further may include one or more valve members 48. Valve member 48 may be a deformable section defined in outer catheter wall 28. In one embodiment, valve member 48 is at least partially defined by a generally triangular shaped slit which is formed in catheter wall 28 adjacent longitudinal lumen 30. In the alternative, valve member 48 may be disposed adjacent longitudinal lumen 32. In one embodiment, valve member 48 is generally triangular with the vertex of the triangle being disposed toward catheter hub 12. Other shapes and configurations different from the triangular shape are also envisioned including, e.g., rectangular, arcuate, diamond-shaped and variations thereof.

Valve member 48 is adapted to move between a substantially closed position (FIGS. 3-5) to a substantially open position (FIG. 6) in response to pressure differential or changes in longitudinal lumen 30. More specifically, valve member 48 may move from the closed position to the open position in response to achieving a predetermined vacuum or negative pressure level in longitudinal lumen 30, such as, e.g., when an occlusion occurs adjacent catheter tip 44. Such occlusion may be in the form of extraneous matter or a clot lodged into longitudinal lumen 30 or the result of positional occlusion of catheter tip 44 with the arterial wall. Once in the open position, valve member 48 permits flow of fluid through opening 50 in catheter wall 28 thus bypassing the occlusion disposed distal of the valve member 48, e.g., adjacent inlet opening 42. Opening 50 is defined by the displaced valve member 48. Thus, valve member 48 may act as a one-way valve adapted to move to the open position upon achieving the predetermined vacuum level in longitudinal lumen 30 of catheter member 14.

Figure 6:
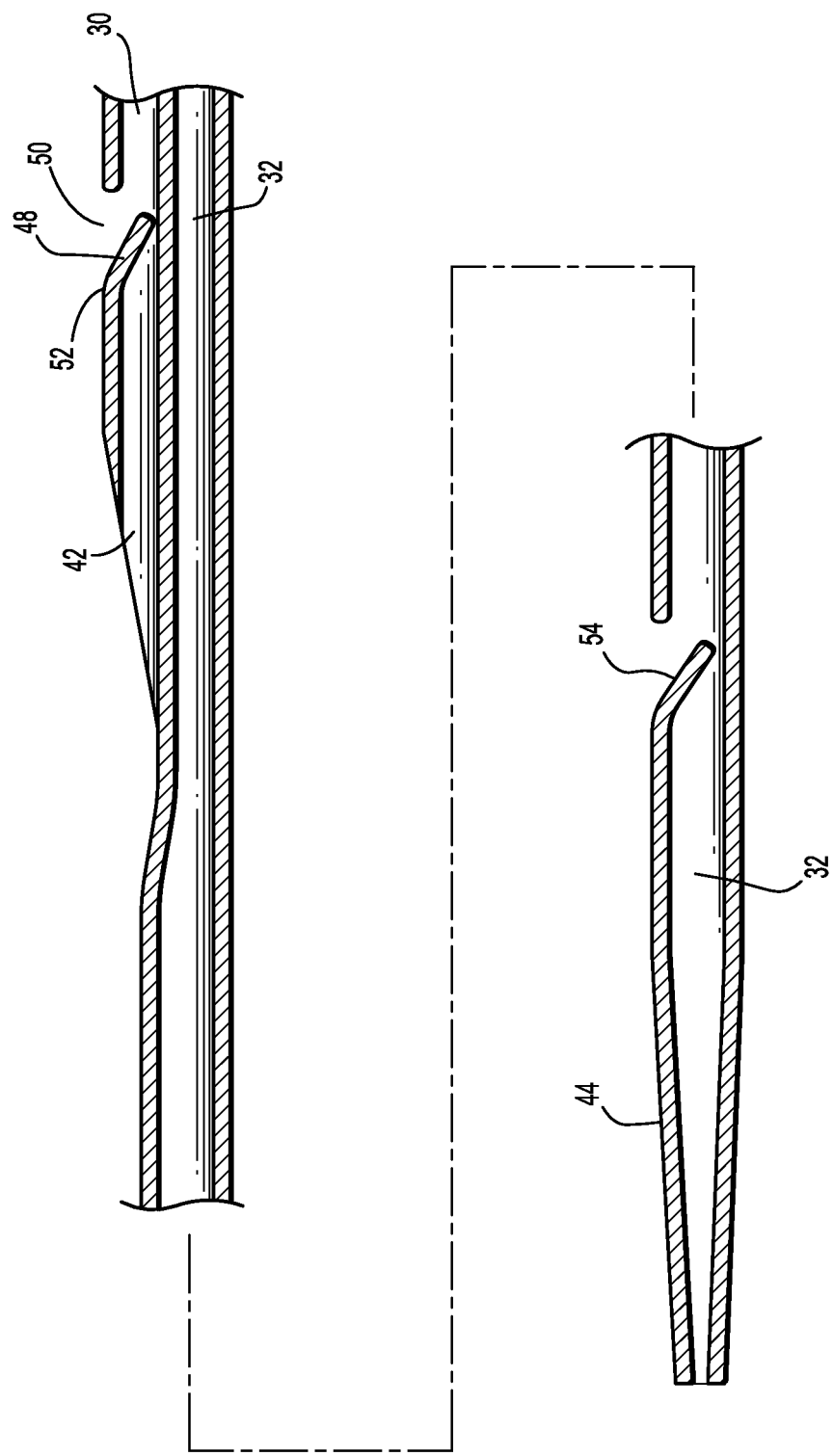
FIG. 6 is a view similar to the view of FIG. 5 illustrating the valve(s) in an open condition.

In one embodiment, valve member 48 pivots between the closed position of FIG. 3 and the open position of FIG. 6 about living hinge 52. In this embodiment, valve member 48 is monolithically formed with catheter wall 28. Other means for pivotally connecting valve member 48 with catheter wall 28 are also envisioned, including, e.g., with the use of a pivot pin or the like. Valve member 48 also may define an area of reduced thickness or cross-section relative to catheter wall 28. Varying the cross-sectional dimension of valve member 48 provides flexibility with respect to the control of threshold values required to open valve member 48.

In one embodiment, leading end 36 of catheter member 10 include a second valve member 54 in fluid communication with longitudinal lumen 32. Second valve member 54 functions in a similar manner to the first-referenced valve member 48, and provides fluid intake or outtake bypass capabilities for longitudinal lumen 32, e.g., when outlet opening 46 is occluded. FIGS. 5 and 6 illustrate second valve member 54 in respective closed and open positions. As a further alternative, leading end 36 of catheter member 10 may be devoid of first valve 48 which would otherwise permit access to longitudinal lumen 30.

Catheter member 14 is preferably flexible and may be formed by conventional injection molding or extrusion means. Outer wall 28 of catheter member 14 may include reinforcing material if desired. Catheter member 14 may have a pre-curved configuration in its normal state, i.e., having a preformed bend which it normally assumes in the absence of an external stressor, to conform to a body cavity or vessel in which the catheter member is to be positioned. Alternatively, catheter member 14 may be devoid of any normally curved orientation.

First and second extension tubes 16, 18 may be any suitable tubing adapted to supply or withdraw fluid to or from a body vessel. First and second extension tubes 16, 18 preferably include a compressible material whereby the tubes 16, 18 may be selectively compressed via clamps 20 to substantially close the opening within the tubes 16, 18. The free or trailing ends of extension tubes 16, 18 remote from catheter hub 12 have adapters 56 mounted thereto. Adapters 56 may be any conventional luer connector or adapter utilized in an environment for administrating fluids. One suitable connection is a luer connector which may incorporate an external thread or cam for securing to a fluid source. Adapters 56 may be secured to extension tubes 16, 18 by any of the aforementioned means including friction or tolerance fit, adhesives, cements, etc.

Clamps 20 are mounted about first and second extension tubes 16, 18. Each clamp 20 is adapted to move from a first open position in non compressive engagement with the respective extension tube 16, 18 to a second substantially closed position to compress the respective extension tube and close the lumen within the tube thereby preventing fluid flow in either direction.

The components of catheter 10 are fabricated from materials suitable for medical applications, such as, for example, polymerics or metals, such as titanium and stainless steel, depending on the particular catheter application and/or preference of a practitioner. Semi-rigid and rigid polymerics are contemplated for fabrication, as well as resilient materials, such as molded medical grade polyurethane, silicone, etc. Any sealing components of catheter 10 may be fabricated from low friction property materials such as polytetrafluoroethylene (PTFE) coated, PTFE impregnated, internally lubricated elastomers, etc. One skilled in the art, however, will realize that other materials and fabrication methods suitable for assembly and manufacture, in accordance with the present disclosure, also would be appropriate.

In use during a hemodialysis application, one adapter 56 (FIG. 1) may be connected to the hemodialysis machine to withdraw blood through, e.g., port or inlet opening 42 into longitudinal lumen 30 and through extension tube 16 for circulation and treatment in the hemodialysis machine. The remaining adapter 56 is intended to return the blood from the hemodialysis machine through extension tube 18 and longitudinal lumen 32 for delivery through outlet opening 46 into the patient. Clamps 20 may be manipulated between their respective first open and second closed positions as desired.

If during the hemodialysis procedure, leading end region 36 of catheter member 14 occludes or thrombus is presented within longitudinal lumen 30, the longitudinal lumen 30 is subjected to increased suction forces while the hemodialysis machine continues to operate. The increased vacuum or negative pressure build up in longitudinal lumen 30 undesirably maintains or increases the occluded condition of catheter tip 44, particularly, in the event of catheter tip occlusion with the vessel wall. However, this increased suction will tend to move or draw valve member 48 to the open position of FIG. 6 thereby permitting passage of fluid through opening 50 in catheter wall 28 and continuance of the hemodialysis procedure. In addition, during passage of fluids through opening 50, pressures within the respective lumen 30, 32 achieve normal operating levels, which desirably results in dislodgement of catheter tip 44 from the vessel wall. In one embodiment, valve member 46 is adapted to open when subjected to a pressure level ranging from about 100 mmHg to about 400 mmHg, and possibly about 250 mmHg. In the event longitudinal lumen 32 is occluded, valve member 54 would open to permit flow of fluid therethrough in a similar manner to valve member 48.

Figure 7:
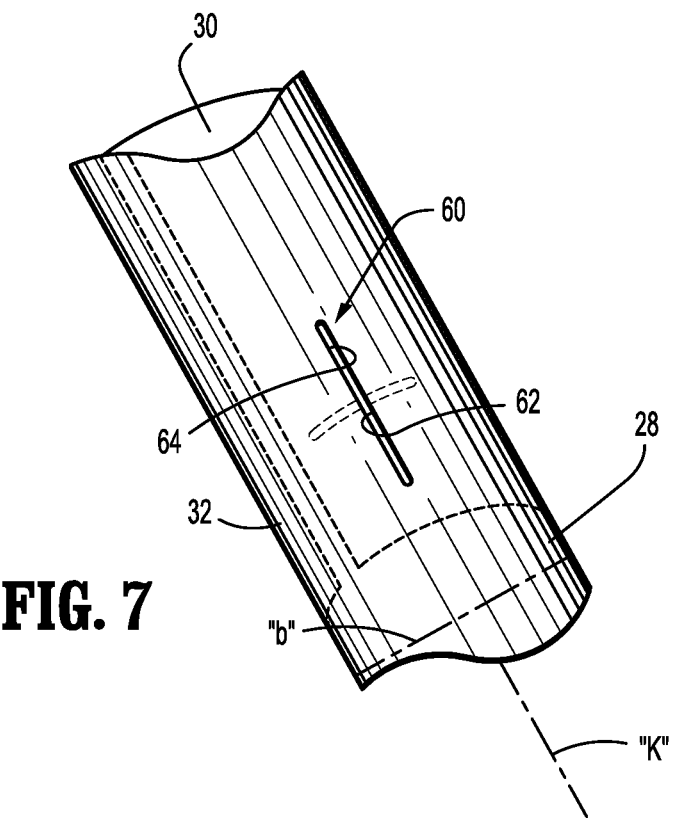
FIG. 7 is a perspective view of the leading end region of an alternate embodiment of the valve of the catheter assembly.

FIG. 7 illustrates another alternate embodiment where the valve member may be in the form of a substantially linear slit 60 defined within catheter member 14 between adjacent inner portions 62, 64 of the catheter member 14. Linear slit 60 may be in a substantially closed position when longitudinal lumen 30 is subjected to a vacuum level below a predetermined or threshold value, and may open via, e.g., through radial inward deflection of inner portions 62, 64 adjacent linear slit 60, when the vacuum level within longitudinal lumen 30 exceeds the threshold level. Linear slit 60 may be arranged in parallel relation with respect to longitudinal axis "k". In the alternative, linear slit 60 may be in general transverse relation to longitudinal axis "k" as depicted in phantom in FIG. 7. Linear slit 60 also may be arranged in oblique relation with respect to the longitudinal axis "k". It is further envisioned that slit 60 may be arcuate in configuration.

Figure 8:
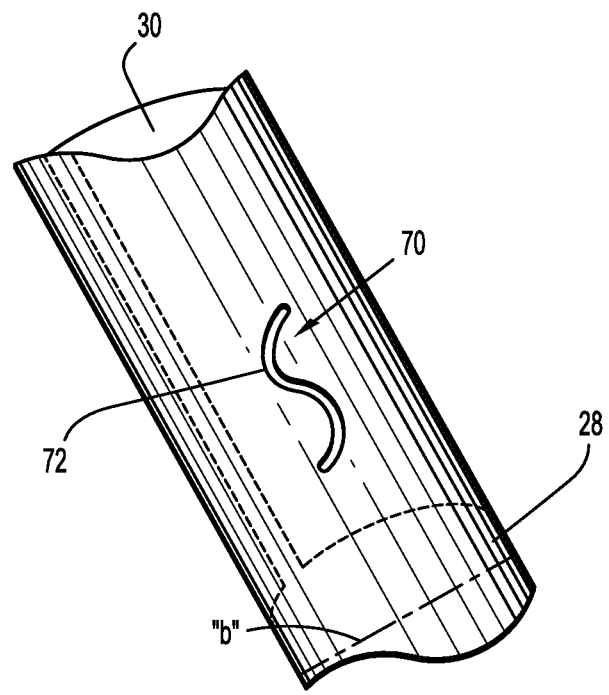
FIG. 8 is a perspective view of the leading end region of another alternate embodiment of the valve of the catheter assembly.

FIG. 8 illustrates another alternate embodiment of the present disclosure. In accordance with this embodiment, catheter member 14 includes valve member 70 in the form of a general sinusoidal-shaped slit 72. Sinusoidal slit 72 may be arranged to oscillate about an axis in general parallel, transverse or oblique relation with respect to longitudinal axis "k". This sinusoidal arrangement increases the effective length and area of slit or valve member 70, which, when opened, may facilitate flow of fluids in either direction through longitudinal lumen 30 and the valve member 70. A sinusoidal slit 72 and valve member 70 may also reduce the threshold suction level required to open the valve member 70 in the event of an occlusion.

Other mechanisms or arrangements to effect the vacuum threshold levels required within longitudinal lumen to open valve member are also envisioned. For example, valve member may have a varied cross-sectional dimension whereby, e.g., the width or thickness of the valve member may be altered to achieve desired characteristics with respect to opening and closure of the valve member.

Figure 9:
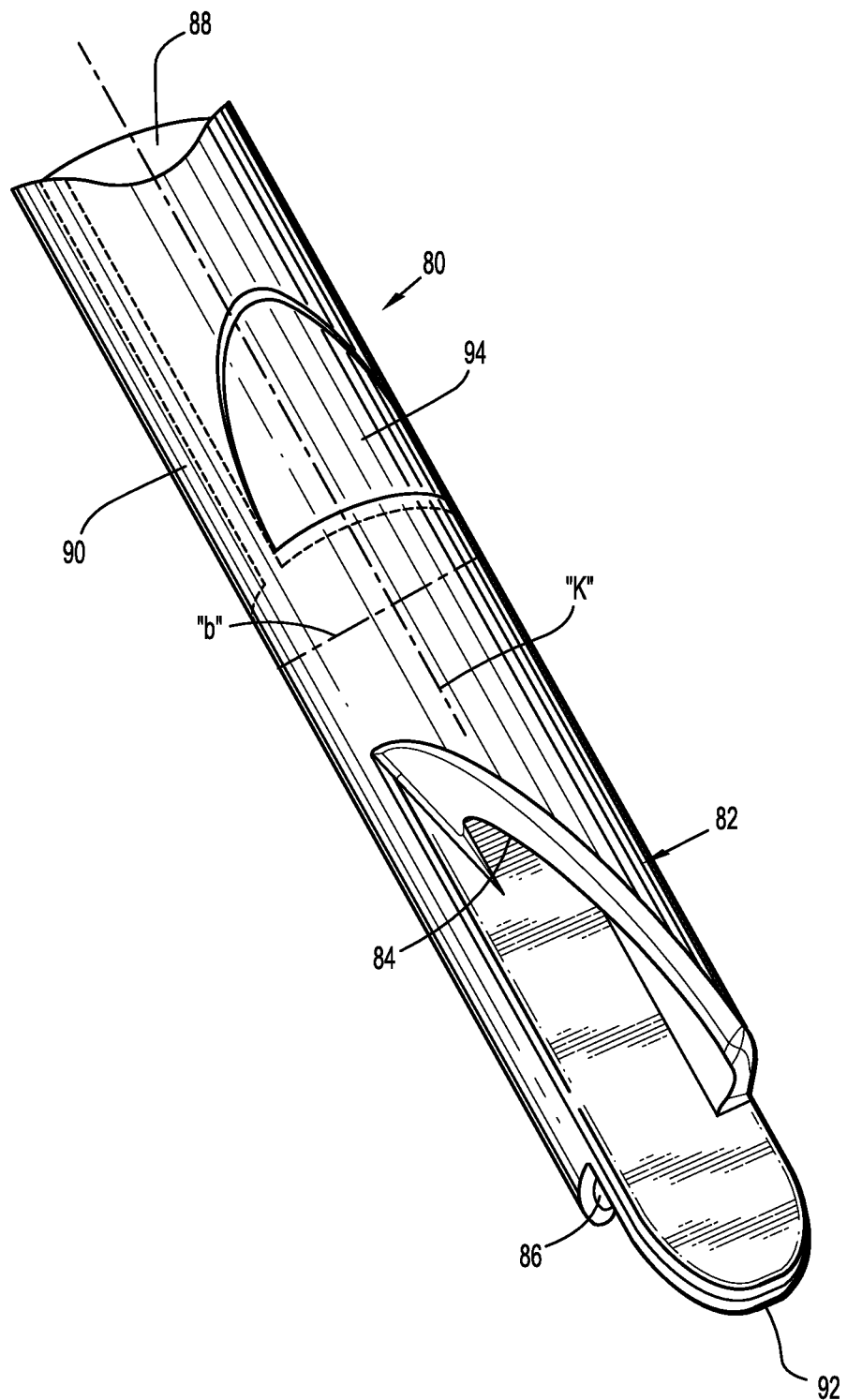
FIG. 9 is a perspective view of another alternate embodiment of the leading end region of the elongate catheter.
Figure 10:
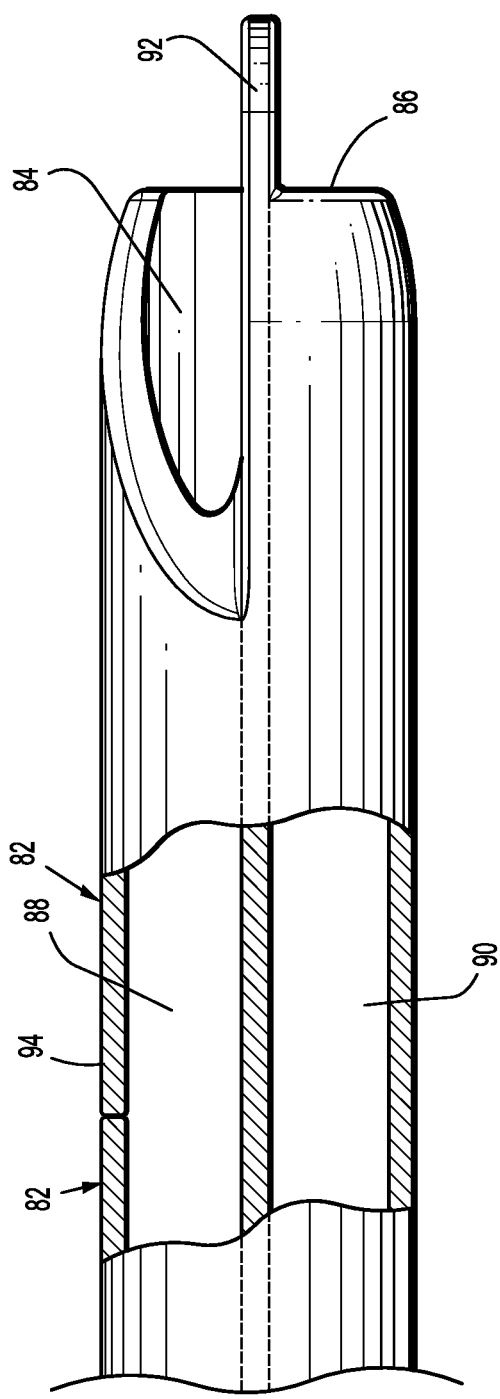
FIG. 10 is a side plan view in partial cross-section of the leading end region of the elongated catheter of FIG. 9 illustrating the valve in a closed position.
Figure 11:
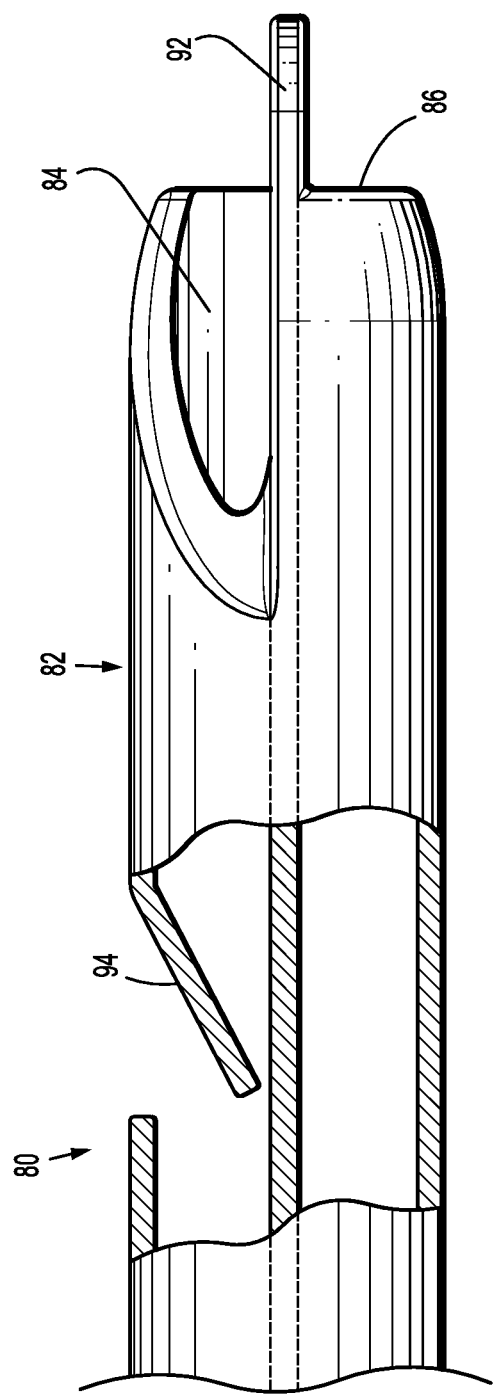
FIG. 11 is a view similar to the view of FIG. 10 illustrating the valve in an open condition.

Referring to FIGS. 9-11, another embodiment of the present disclosure is illustrated. Catheter member 80 includes leading or distal end region 82. This embodiment of distal end region 82 is disclosed in commonly assigned U.S. Pat. No. 7,182,746 to Haarala, the entire contents of which are hereby incorporated herein by reference. Leading end region 82 includes a pair of opposed openings or ports 84,86 arranged in its outer wall in diametrical relation and in fluid communication with respective first and second longitudinal lumens 88, 90. Each opening 84, 86 is spaced from catheter tip 92. Each opening 84, 86 may be characterized by having an arcuate or spiraled recessed wall surface to define a partial generally arcuate opening as shown. Openings 84, 86 permit passage of fluids during the procedure. Leading end region 82 includes one or more valve members 94 substantially similar in design and operation to any of the aforedescribed embodiments. Valve member 94 moves between the closed position of FIG. 9 and the open condition of FIG. 11 in response to an excessive vacuum or negative pressure draw within either lumen 88, 90.

Figure 12:
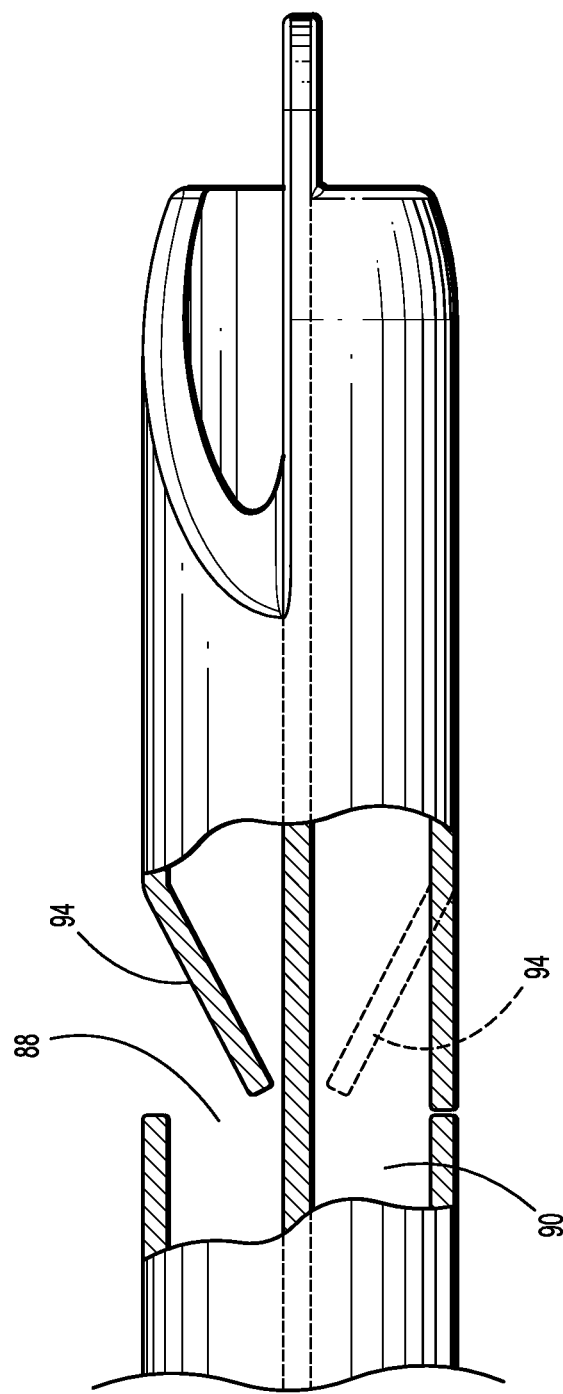
FIG. 12 is a side plan view in partial cross-section of an alternate embodiment of the leading end region of the elongate catheter.
Figure 13:
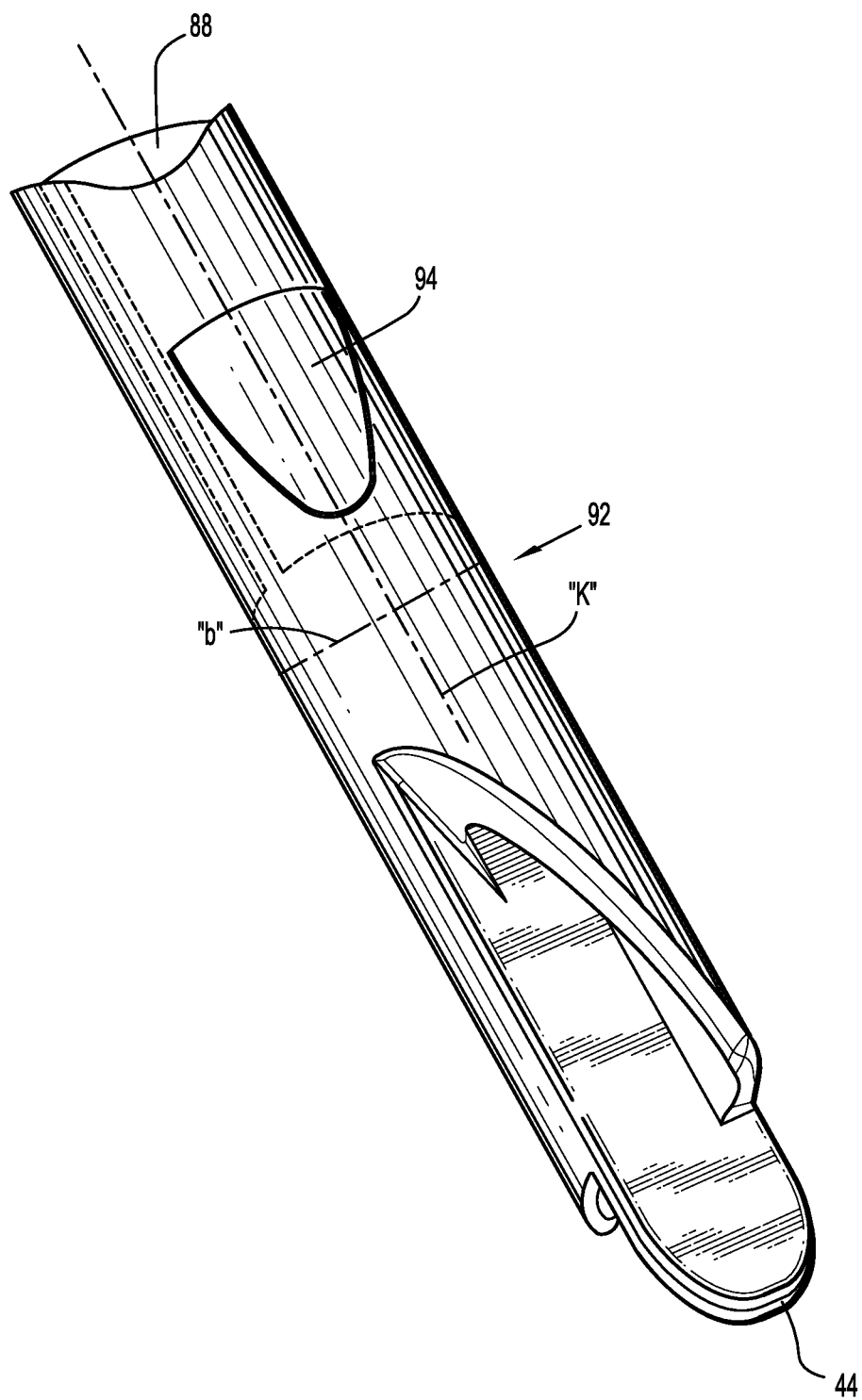
FIG. 13 is a perspective view of another embodiment of the elongated catheter assembly.

FIG. 12 illustrates an alternative embodiment where at least one valve member 94 is in fluid connection with each longitudinal lumen 88, 90. FIG. 13 illustrates an alternate embodiment of leading end region 92 in which the orientation of valve member 94 is reversed with the vertex of the triangular shaped slit facing catheter tip 44. This arrangement may reduce the level of the suction force or negative pressure required to move valve 94 to the open position.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A medical catheter assembly, which comprises:
   an elongated catheter member defining a longitudinal axis and at least one lumen for passage of fluid, and having proximal and distal end regions, the distal end region having an open end; and
   a valve disposed adjacent the distal end region of the catheter member, the valve adapted to move from a closed position to an open position in response to a predetermined vacuum pressure level within the at least one lumen when the open end is at least partially occluded to permit flow of the fluid through the valve and into the at least one lumen.

2. The catheter assembly according to claim 1 wherein the catheter member includes a fluid port in communication with the at least one lumen and distal of the valve, the valve being adapted to move to the open position in the event of an at least partial luminal occlusion within the at least one lumen at locations distal of the valve.

3. The catheter assembly according to claim 2, wherein the valve includes a deformable section adjacent the distal end region of the catheter member, the deformable section being configured to deform upon achieving the predetermined vacuum level in the at least one lumen of the catheter member.

4. The catheter assembly according to claim 2 wherein the valve includes a one-way pressure relief member adapted to move to the open position upon achieving the predetermined vacuum level in the at least one lumen of the catheter member.

5. The catheter assembly according to claim 2, wherein the catheter member includes an outer catheter wall, the outer wall having inner portions defining a slit therein whereby the inner portions are adapted for relative movement to move between the open position and the closed position.

6. The catheter assembly according to claim 5, wherein the inner portions of the catheter wall define a substantially linear slit.

7. The catheter assembly according to claim 5, wherein the inner portions of the catheter wall define a substantially sinusoidal slit.

8. The catheter assembly according to claim 2 wherein the catheter includes a second lumen and a second valve, the second valve adapted to move from a closed position to an open position in response to a predetermined vacuum pressure level within the second lumen to permit flow of the fluid through the second valve and the second lumen.

9. The catheter assembly according to claim 8 wherein the catheter member includes a second fluid port in communication with the second lumen and distal of the second valve.

10. The catheter assembly according to claim 2 wherein the valve is arranged to define an opening within the catheter wall when the valve is in the open position.

11. The catheter assembly according to claim 1, wherein the catheter member includes an outer catheter wall, the valve being a flap defined within the outer catheter wall.

12. The catheter assembly according to claim 11, wherein the outer catheter wall and the flap are monolithically formed.

13. The catheter assembly according to claim 12 wherein the flap is generally triangular in shape.

14. A dialysis catheter, which comprises:
   an elongate catheter member including an outer wall member defining proximal and distal end regions and a longitudinal axis, the distal end region having an open end, the outer wall member having first and second longitudinal lumens and including first and second ports in respective fluid communication with the first and second longitudinal lumens, the first port and the first lumen defining an inflow passage for removal of blood under vacuum for circulation within a hemodialysis machine, the second port and the second longitudinal lumen defining an outflow passage for return of the blood from the hemodialysis machine; and a valve disposed relative to the outer wall member proximal of the first port, the valve adapted to move from a closed position to an open position in response to a predetermined vacuum pressure level realized within the first longitudinal lumen when the open end of the distal end region is at least partially occluded to permit flow of blood through the valve and into the first longitudinal lumen.

15. The catheter assembly according to claim 14 wherein the valve is adapted to move to the open position in the event of an at least partial luminal occlusion within the first longitudinal lumen at locations distal of the valve.

16. The catheter assembly according to claim 14 wherein the valve includes a flap defined in the outer wall member of the catheter member.

17. The catheter assembly according to claim 16 wherein the flap is adapted to move about a living hinge between the closed position and the open position.

18. The hemodialysis catheter assembly according to claim 14 including a second valve disposed relative to the outer wall member proximal of the second port, the second valve adapted to move from a closed position to an open position in response to a predetermined vacuum pressure level realized within the second longitudinal lumen to permit flow of the fluid through the second valve.

* * * * *